US010830752B2

(12) United States Patent
Romero-Sarmiento et al.

(10) Patent No.: US 10,830,752 B2
(45) Date of Patent: Nov. 10, 2020

(54) METHOD FOR ESTIMATING THE QUANTITY OF FREE HYDROCARBONS IN A SAMPLE OF SEDIMENTARY ROCK

(71) Applicant: IFP Energies nouvelles, Rueil-Malmaison (FR)

(72) Inventors: Maria-Fernanda Romero-Sarmiento, Rueil-Malmaison (FR); Said Youssouf, Poissy (FR); Geremie Letort, Vienne (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 170 days.

(21) Appl. No.: 16/154,218

(22) Filed: Oct. 8, 2018

(65) Prior Publication Data

US 2019/0107522 A1 Apr. 11, 2019

(30) Foreign Application Priority Data

Oct. 9, 2017 (FR) ...................................... 17 59447

(51) Int. Cl.
  *G01N 31/12* (2006.01)
  *G01N 33/24* (2006.01)
(52) U.S. Cl.
  CPC .................................. *G01N 33/241* (2013.01)
(58) Field of Classification Search
  CPC .... G01N 33/241; G01N 25/00; G01N 33/004; G01N 2203/0694; G01N 33/0047;
  (Continued)

(56) References Cited

U.S. PATENT DOCUMENTS

| 3,953,171 A | 4/1976 | Espitalie et al. |
| 4,352,673 A | 10/1982 | Espitalie et al. |

(Continued)

FOREIGN PATENT DOCUMENTS

| EP | 0691540 B1 | 2/2003 |
| FR | 2227797 A5 | 11/1974 |

(Continued)

OTHER PUBLICATIONS

Huairen Cao et al: "Shale Oil Assessment for the Songliao Basin, Northeastern China, Using Oil Generation-Sorption Method", Energy & Fuels., vol. 31, No. 5, (Apr. 10, 2017), pp. 4826-4842, XP055488161.

(Continued)

*Primary Examiner* — Brandi N Hopkins
(74) *Attorney, Agent, or Firm* — Fitch, Even, Tabin & Flannery LLP

(57) ABSTRACT

A method for determining a parameter representative of a quantity of hydrocarbon-containing compounds present in free form within a sedimentary rock, wherein a first sample representative of the sedimentary rock is obtained and a second sample which is representative of isolated total organic matter in the sedimentary rock is obtained by eliminating a free mineral portion part of the second sample. Each of the samples are processed according to steps comprising heating the sample according to a first heating sequence under an inert atmosphere, and continuously measuring a representative quantity of the hydrocarbon-containing compounds released during at least a part of the first heating sequence. A representative quantity of CO and a representative quantity of $CO_2$ released during a second heating sequence is measured. The parameter representative of the quantity of hydrocarbon-containing compounds present in free form within the sedimentary rock from the first and second samples is determined.

33 Claims, 5 Drawing Sheets

(58) Field of Classification Search
CPC .......... G01N 1/44; G01N 1/34; G06F 19/701; G01V 99/005; G01V 2210/661; G01V 99/00; G01V 9/005; E21B 49/00; G16C 10/00; B09C 1/065; B09C 1/005; B09B 3/0083

See application file for complete search history.

(56) References Cited

U.S. PATENT DOCUMENTS

| | | | |
|---|---|---|---|
| 5,811,308 A * | 9/1998 | Espitalie | G01N 33/241 436/145 |
| 5,843,787 A * | 12/1998 | Trabelsi | G01N 33/241 436/139 |
| 5,866,814 A * | 2/1999 | Jones | E21B 49/00 73/152.11 |
| 7,772,004 B2 * | 8/2010 | Lorant | G01N 33/241 436/32 |
| 9,495,488 B2 * | 11/2016 | Jones | G06F 30/20 |
| 2015/0346179 A1 | 12/2015 | Pillot et al. | |
| 2016/0098543 A1 | 4/2016 | Salmon et al. | |

FOREIGN PATENT DOCUMENTS

| | | |
|---|---|---|
| FR | 2472754 A1 | 7/1981 |
| FR | 3021749 A1 | 12/2015 |

OTHER PUBLICATIONS

Johannes et al: "Evaluation of oil potential and pyrolysis kinetics of renewable fuel and shale samples by Rock-Eval analyzer", Journal of Analytical and Applied Pyrolysis, Elsevier BV, NL, vol. 79, No. 1-2, (Apr. 19, 2007), pp. 183-190, XP022062360.
Preliminary Search Report for FR 1759447 dated Jun. 27, 2018.

* cited by examiner

METHOD FOR ESTIMATING THE QUANTITY OF FREE HYDROCARBONS IN A SAMPLE OF SEDIMENTARY ROCK

CROSS REFERENCE TO RELATED APPLICATIONS

Reference is made to French Application No. 17/59.447 filed Oct. 9, 2017, which is incorporated herein by reference in its entirety.

BACKGROUND OF THE INVENTION

Field of the Invention

The present invention relates to the oil industry, and more particularly the field of the exploration and exploitation of a geological formation in which hydrocarbons are trapped. More specifically, the present invention improves the characterization of the oil potential of a sedimentary rock such as a source rock in which unconventional hydrocarbons are trapped.

Description of the Prior Art

The compounds of oil, principally hydrocarbons that can be extracted by means of organic solvents, are formed by the conversion of insoluble organic matter (called kerogen) caused by the rise in temperature associated with the burial of sediments in a sedimentary basin. Sedimentary rocks that have given rise to oil are called source rocks. Under certain conditions, a portion of the oil thus formed will be expelled from the source rock, then will migrate to rocks called reservoir rocks, in which it will accumulate.

Source rocks have long been considered as an unexploitable source of hydrocarbons. With the development of exploration and exploitation technologies, hydrocarbons from source rocks today constitute a new source of fossil energy. For this type of hydrocarbons, the source rock is also a reservoir rock, the hydrocarbons remaining trapped, disseminated within a rock with very low permeability. Hydrocarbons from source rocks are categorized in the family of unconventional hydrocarbons, the extraction thereof requiring unconventional techniques with respect to the techniques currently used by the oil and gas industry. This type of source rock is known as hydrocarbon source rock, or also unconventional source rock, and are most often called "shale plays".

Generally, knowledge of the soluble organic matter (oil) on the one hand, and the insoluble organic matter (kerogen) on the other hand, present in a rock sample is of great interest for oil exploration and exploitation. In fact, it is known for example that:
  the quantity of oil formed in sediments increases steadily with the burial depth, due to the Earth's thermal gradient. From this, it is possible to estimate the level of evolution of the organic matter contained in these sediments and, more particularly, the interval of evolution which corresponds to the main phase of the formation of oil.
  the nature of the insoluble organic matter contained in the rocks conditions the petroligenous potential of these rocks, that is their greater or lesser capacity for producing oil.

In a source rock (in the broad sense), the hydrocarbons can be found trapped either in free form (in the fracture porosity or the matrix porosity) or in retained form (retained on the organic matter or the shale mineral matrix).

Adsorption is a retention mechanism, by trapping on the surface of very small-scale solids. The capacities of adsorption of a gas onto a solid depend on the temperature and the pressure, but also to a large extent on the nature of the gas and on the composition of the solid itself. With regard to the source rocks, it is the organic matter which has the greatest adsorption capacities. Coal, in particular, has a vast adsorption capacity and a very large part of the coal bed methane is naturally stored in the rock by means of this process. Clays, which on a small scale are composed of a large number of layers, have a large specific surface and therefore large adsorption capacities. It should be noted that by reducing the temperature or the pressure to which a rock is subjected, the trapped hydrocarbons can be desorbed and produced.

In the case of an unconventional source rock, it is particularly important to reliably estimate the quantity of free hydrocarbons produced by this source rock, as this quantity represents the quantity of hydrocarbons that are present in this rock and that are potentially recoverable. Thus, having access to such information makes it possible to identify the oil potential of the unconventional source rock being studied, which contributes to the decision whether or not to exploit this source rock.

In general terms below:
  by "free hydrocarbons" it is hydrocarbon-containing compounds which are contained in the sedimentary rocks without any chemical and/or physical retention;
  by "retained hydrocarbons" it is hydrocarbon-containing compounds which are at least one of trapped and adsorbed by at least one of chemical and physical bonds in the porous matrices of the organic matter;
  by "light thermovaporizable hydrocarbons or hydrocarbon-containing compounds with a low molecular weight" it is hydrocarbons having a number of carbon atoms which is less than 20, as described in the document (Romero-Sarmiento et al. 2016);
  by "heavy thermovaporizable hydrocarbons or hydrocarbon-containing compounds with a high molecular weight" it is hydrocarbons in which the number of carbon atoms is comprised between 20 and 30, as described in the document (Romero-Sarmiento et al. 2016);
  by "very heavy thermovaporizable hydrocarbons or hydrocarbon-containing compounds with a very high molecular weight" it is hydrocarbons in which the number of carbon atoms is greater than 30, as described in the document (Romero-Sarmiento et al. 2016);
  by "Total Organic Carbon" it is the percentage (expressed by weight) of organic matter present in the rock. The higher this value, the more hydrocarbons a source rock can generate. A rock is considered to be a source rock if this value is greater than 1%. Above 3%, it is a good source rock, and above 5%, it is an excellent source rock.

STATE OF THE ART

The following documents will be cited in the course of the description:
Behar F., Beaumont V., De B., Penteado H. L. (2001) Rock-Eval 6 Technology: Performances and Developments, Oil & Gas Science and Technology 56, 111-134.

Durand, B., Nicaise, G., 1980. Procedure for Kerogen Isolation. In: Durand, B. (Ed.), Kerogen, Insoluble Organic Matter from Sedimentary Rocks. Editions Technip, Paris, pp. 35-53.

Romero-Sarmiento, M.-F., Euzen T., Rohais S., Jiang C., Littke R. (2016). Artificial Thermal Maturation of Source Rocks at Different Thermal Maturity Levels: Application to the Triassic Montney and Doig Formations in the Western Canada Sedimentary Basin. Organic Geochemistry 97: 148-162.

The ROCK-EVAL® device (IFP Energies nouvelles, France) developed by the applicant is known, and is described in particular in the documents FR 2227797 and corresponding to U.S. Pat. No. 3,953,171 and FR 2472754 and corresponding to U.S. Pat. No. 4,352,673. The ROCK-EVAL device allows pyrolysis in an inert atmosphere (non-oxidizing, according to a predefined sequence of temperatures of a sample, for example of sedimentary rock). The pyrolysis furnace cooperates with a device for detecting and measuring the quantity of hydrocarbon-containing compounds of the pyrolyzed sample. The specific detection device comprises, for example, a detector of the flame ionization type, conventionally used in analyses by gas phase chromatography. The detector delivers a signal representing the measured quantities of hydrocarbon-containing products. This signal can be transmitted to a device for providing calculation, storage and display in which a specific item of software calculates, displays and stores the different parameters representing the characteristics of the hydrocarbons present.

Thus, the ROCK-EVAL device makes it possible in particular to measure the quantity of hydrocarbon-containing compounds released during pyrolysis. A pyrogram can then be created, which is a curve showing the change in the quantity of hydrocarbon-containing compounds released, with respect to the weight of the sample in question, as a function of time. A pyrogram generally has several peaks (cf. for example the peaks in FIG. 2) that are generally well differentiated. From the surface area of one of these peaks, a value representative of the quantity of hydrocarbon-containing compounds released during the temperature range on either side of the peak in question is obtained. Accurate information can also be obtained about the quantity of total organic carbon (TOC) and the quantity of mineral carbon (MinC) contained in a rock sample.

The method called the "Basic" method (also known as "Bulk Rock" method) that can be implemented with the ROCK-EVAL® device, and dedicated more particularly to samples of source rock, is known. This method is in particular described in the document (Behar et al., 2001). The sequence of temperatures of this method is characterized by an initial temperature T1 of the pyrolysis furnace generally comprised between 300° C. and 350° C., a temperature which is maintained for a predetermined duration of a few minutes. It is during this phase that the hydrocarbons called "free" hydrocarbons (corresponding in reality to hydrocarbons of low to high molecular weight) initially contained in the rock sample are released. The quantity thereof is estimated by measuring the surface area of a first peak, denoted $S_1$. Then, the pyrolysis temperature is increased progressively up to a temperature T2, generally of 650° C. During this phase, the volatilization of the very heavy hydrocarbon-containing compounds takes place, as well as the cracking of the non-volatile organic matter (kerogen). The quantity of hydrocarbon-containing compounds released during this phase of thermal cracking is estimated by measuring the surface area of a second peak, denoted $S_2$. It corresponds to the quantity of hydrocarbon-containing compounds which would have been generated if the rock had reached a sufficient stage of maturity.

The method called the "Reservoir" method that can also be implemented with the ROCK-EVAL® device and dedicated more particularly to samples of reservoir rock and oils, is also known. This method is in particular described in the document EP 0691540 B1 and corresponding to U.S. Pat. No. 5,843,787. The sequence of temperatures of the "Reservoir" method is characterized by an initial temperature T1 of the pyrolysis furnace that is less than 200° C., and preferentially equal to 180° C. This temperature is maintained for a predetermined duration and the quantity of light hydrocarbon-containing compounds is estimated by measuring the surface area of a first peak, denoted $S_{1r}$. Then the temperature of the pyrolysis furnace is raised to a second temperature T2 of approximately 370° C., during the course of which phase the quantity of heavier hydrocarbons released is estimated by estimating the surface area of a second peak, denoted $S_{2a}$. The temperature T2 corresponds substantially to the end of the thermovaporization of certain hydrocarbons and to the start of pyrolitic cracking of the heavy compounds. Thus, the family of hydrocarbon-containing compounds corresponding to the peaks $S_{1r}$ and $S_{2a}$ of the "Reservoir" method is almost equivalent to the family of characteristic hydrocarbon-containing compounds of the peak $S_1$ of the "Basic" method, that is hydrocarbons of low to high molecular weight. Then the pyrolysis temperature is increased again up to a third temperature T3 of a maximum 650° C. The surface area of a third peak, denoted $S_{2b}$, representative of the heavy hydrocarbon-containing compounds, is estimated during this third phase of heating. This peak $S_{2b}$ can be considered as equivalent to the peak $S_2$ of the "Basic" method.

More recently, the method called the "Shale Play" method has been developed, described in particular in patent FR 3021749 and corresponding to US published patent application 2015/0346179, and is also able to be implemented with the ROCK-EVAL® device. It is a method allowing an accurate quantification of the light to heavy hydrocarbons contained in a sedimentary rock, such as an unconventional source rock. This method has in particular been developed since it has become apparent that the "Basic" and "Reservoir" methods underestimate the surface area of the peak or peaks corresponding to the hydrocarbons called free hydrocarbons (in reality the quantity of hydrocarbon-containing compounds of low to high molecular weight) contained in a given rock sample. An implementation of the sequence of temperatures of the Shale Play method is shown in FIG. 1. Thus, the temperature sequence of the "Shale Play" method is a succession of three heating steps (ramps corresponding to segments A, C and E in FIG. 1), separated by two temperature maintenance steps (isothermal plateaus corresponding to segments B and D in FIG. 1), allowing the differentiated release of light, heavy and very heavy hydrocarbon-containing compounds. More precisely, the temperature sequence of the "Shale Play" method starts at a low first temperature (T1), comprised between 50 and 120° C., which makes it possible to measure more completely the quantity of hydrocarbon-containing compounds called free hydrocarbon-containing compounds (in reality of low to high molecular weight) present in a sample. In addition, as the method according to the invention contains, between two heating steps (cf. ramps A, C and E in FIG. 1), temperature holding steps (cf. isothermal plateau B corresponding to a temperature T2 comprised between 180 and 220° C., and isothermal plateau D, corresponding to a temperature T3 comprised between 330° C. and 370° C., in FIG. 1) ensuring that the thermovaporization of the thermovaporizable hydrocarbon-containing compounds is complete within the temperature range in question.

FIG. 2 shows an example of a pyrogram recorded during the heating sequence under an inert atmosphere as described in FIG. 1. In this figure, the presence of three peaks can be seen, denoted $S_{h0}$, $S_{h1}$ and $S_{h2}$, that are representative of the quantity of hydrocarbon-containing compounds released during the different heating steps. More precisely, the peak $S_{h0}$ corresponds to the quantity of hydrocarbon-containing compounds released between the first temperature T1 and the second temperature T2, that is during segments A and B in FIG. 1. This peak $S_{h0}$ is representative of the lightest thermovaporizable hydrocarbons. The peak $S_{h1}$ corresponds to the quantity of hydrocarbon-containing compounds released between the second temperature T2 and the third temperature T3, that is during segments C and D in FIG. 1. This peak $S_{h1}$ is representative of the heavy thermovaporizable hydrocarbons. The peak $S_{h2}$ corresponds to the quantity of hydrocarbon-containing compounds released between the third temperature T3 and the fourth temperature T4, that is during segment E in FIG. 1. This peak $S_{h2}$ is representative of the very heavy thermovaporizable hydrocarbons.

It should be noted that the method described in the patent application FR 3021749 and corresponding to US published patent application 2015/0346179 establishes that the quantity of free hydrocarbon-containing compounds can be represented by the sum of the value $S_{h0}$ and the value $S_{h1}$. In reality, it is very clear to those working in the field that the quantity of compounds measured by the peaks $S_{h0}$ and $S_{h1}$ represents a total quantity of hydrocarbon-containing compounds, comprising both the quantity of hydrocarbon-containing compounds, from low to high molecular weight, that are actually free and the quantity of hydrocarbon-containing compounds, from low to high molecular weight, that are retained in the organic matter.

Thus, the method described in patent application FR 3021749 and corresponding to US published patent application 2015/0346179 does not make it possible to distinguish between the free hydrocarbons part and the part with hydrocarbons retained in the organic matter. Due to the increasing interest in hydrocarbons from source rocks, it appears essential to be able to make such a quantitative distinction.

SUMMARY OF THE INVENTION

The present invention improves the estimation of free hydrocarbons within an unconventional source rock. More precisely, the present invention quantifies in a differentiated manner the quantity of free hydrocarbons from the quantity of hydrocarbons retained in the organic matter of the rock. Such a distinction is in fact necessary in order to estimate the hydrocarbons that are actually available and could potentially be produced.

In particular, the present invention is based on the implementation of a first complete artificial maturation (comprising a pyrolysis step followed by an oxidation step) on a rock sample from the geological formation being studied and a second complete artificial maturation on a sample of the isolated total organic matter contained in the rock being studied.

The invention is a method for determining a parameter representative of a quantity of hydrocarbon-containing compounds present in free form within a sedimentary rock, from a first sample representative of the rock and from a second sample representative of the total organic matter isolated from the rock.

The method comprises at least the application of the following steps for each of said samples:

A. heating the sample according to a first heating sequence under an inert atmosphere, and continuously measuring a representative quantity of the hydrocarbon-containing compounds released during at least a part of the first heating sequence, a representative quantity of CO and a representative quantity of $CO_2$ released during the first heating sequence;

B. heating a residue of the sample originating from the first heating sequence according to a second heating sequence under an oxidizing atmosphere, and measuring a representative quantity of CO and a representative quantity of $CO_2$ released during the second heating sequence.

Then, according to the invention the parameter representative of the quantity of hydrocarbon-containing compounds present in free form within the rock is determined from at least the measurements carried out for the first and second samples.

According to an implementation of the invention, at the end of steps A and B applied at least to the first and the second sample, it is possible to determine:

i. for each of the samples, a level of total organic carbon from the measurements of the quantity of $CO_2$ and CO carried out during the first and second heating sequences;

ii. a parameter representative of a quantity of hydrocarbon-containing compounds present in the first sample in both a free and a retained form, from at least the measurement of the representative quantity of the hydrocarbon-containing compounds released during the part of the first heating sequence applied to the first sample, and of the level of total organic carbon determined for the first sample;

iii. a parameter representative of a quantity of hydrocarbon-containing compounds present in the second sample in retained form, from at least the measurement of the representative quantity of the hydrocarbon-containing compounds released during the part of the first heating sequence applied to the second sample, and of the level of total organic carbon determined for the second sample;

and it is possible to determine the parameter representative of the quantity of hydrocarbon-containing compounds present in free form in the rock from the difference between the parameter representative of the quantity of hydrocarbon-containing compounds present in the first sample in both a free and a retained form and at least the parameter representative of the quantity of hydrocarbon-containing compounds present in the second sample in retained form.

According to an embodiment variant of the invention, the second heating sequence under an oxidizing atmosphere applied to one of the residues of one of the first and second samples can comprise at least the following step: starting from a temperature comprised between 200° C. and 400° C., the temperature of the residue is raised according to a temperature gradient comprised between 20 and 40° C./minute, up to a temperature comprised between 750 and 950° C.

According to an implementation of the invention, it is possible to determine the parameter representative of the quantity of hydrocarbon-containing compounds present in the first sample in both a free and a retained form according to a formula of the type:

$$HC_{Total,rock} = \frac{SurfQ_{rock}}{m_{rock} * TOC_{rock}}$$

where $SurfQ_{rock}$ corresponds to at least a part of the area under the measurement curve of the quantity of hydrocarbon-containing compounds released by the first sample, $m_{rock}$ corresponds to the initial mass of the first sample, and $TOC_{rock}$ is the level of total organic carbon determined for the first sample.

According to an implementation of the invention, it is possible to determine the parameter representative of the quantity of hydrocarbon-containing compounds present in the second sample in retained form according to a formula of the type:

$$HC_{Sorbed,TOM} = \frac{SurfQ_{TOM}}{m_{TOM} * TOC_{TOM}}$$

where $SurfQ_{TOM}$ corresponds to at least a part of the area under the measurement curve of the quantity of hydrocarbon-containing compounds released by the second sample, $m_{TOM}$ corresponds to the initial mass of the second sample, and $TOC_{TOM}$ is the level of total organic carbon determined for the second sample.

According to an implementation of the invention, the first heating sequence under an inert atmosphere applied to a sample selected from the first sample and the second sample can comprise at least the following steps:

a) starting from a first temperature value (T1) comprised between 50° C. and 120° C., raising the temperature of the sample according to a first temperature gradient comprised between 1° C./min and 50° C./min, up to a second temperature value (T2) comprised between 180° C. and 220° C., and the sample is maintained at the second temperature value (T2) during a first predetermined duration;

b) starting from the second temperature value (T2), raising the temperature of the sample according to a second temperature gradient comprised between 1° C./min and 50° C./min, up to a third temperature value (T3) comprised between 330° C. and 370° C., and maintaining the sample at the third temperature value (T3) during a second predetermined duration;

c) starting from the third temperature value (T3), raising the temperature of the sample according to a third temperature gradient comprised between 1° C./min and 50° C./min, up to a fourth temperature value (T4) comprised between 630° C. and 670° C.

According to an implementation of the invention, at the beginning of step a), the sample can be maintained at the first temperature T1 for a duration comprised between 2 and 6 minutes.

According to an implementation of the invention, the first and second durations can be comprised between 2 and 4 minutes.

According to an implementation of the invention, the parameter representative of the quantity of hydrocarbon-containing compounds present in free form in the first sample can be determined according to a formula of the type:

$$HC_{Total,rock}^{Shx} = \frac{SurfShx_{rock}}{m_{rock} * TOC_{rock}},$$

with Shx selected from {Sh0,Sh1,Sh0+Sh1}, where $SurfSh0_{rock}$, $SurfSh1_{rock}$ and $SurfSh0+Sh1_{rock}$ correspond respectively to the area under the measurement curve of the quantity of hydrocarbon-containing compounds released by the first sample between the first and second temperatures, the second and third temperatures, and the first and third temperatures.

According to an implementation of the invention, the parameter representative of the quantity of hydrocarbon-containing compounds present in retained form in the second sample can be determined according to a formula of the type:

$$HC_{Sorbed,TOM}^{Shx} = \frac{SurfShx_{TOM}}{m_{TOM} * TOC_{TOM}},$$

with Shx selected from {Sh0,Sh1,Sh0+Sh1}, where $SurfSh0_{TOM}$, $SurfSh1_{TOM}$ and $SurfSh0+Sh1_{TOM}$ correspond respectively to the area under the measurement curve of the quantity of hydrocarbon-containing compounds released by the second sample between the first and second temperatures, the second and third temperatures, and the first and third temperatures.

According to an implementation of the invention, the parameter representative of the quantity of hydrocarbon-containing compounds present in free form in the rock can be determined according to a formula of the type:

$HC_{Free}^{Shx} = HC_{Total,rock}^{Shx} - HC_{Sorbed,TOM}^{Shx}$, with Shx selected from {Sh0, Sh1, Sh0+Sh1}, According to an implementation of the invention, a parameter representative of the proportion of the quantity of hydrocarbon-containing compounds present in free form with respect to the quantity of hydrocarbon-containing compounds present in retained form in the rock can also be determined according to a formula of the type:

% $HC_{Free}^{Shx} = HC_{Free}^{Shx}/HC_{Total,rock}^{Shx} * 100$, with Shx selected from {Sh0, Sh1, Sh0+Sh1}.

BRIEF DESCRIPTION OF THE DRAWINGS

Other characteristics and advantages of the method according to the invention will become apparent on reading the following description of non-limitative embodiment examples, with reference to the attached figures which are described below.

DETAILED DESCRIPTION OF THE INVENTION

Figure 1:
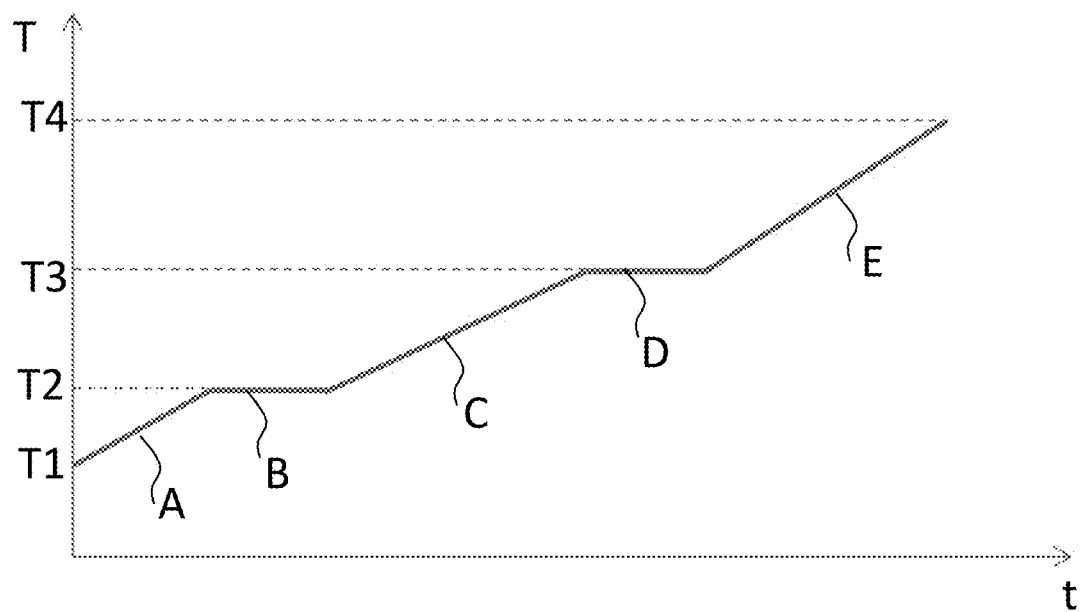
FIG. 1 shows a preferred variant of a heating sequence under an inert atmosphere of the method according to the invention.

The subject matter of the present invention is a method for reliably estimating the quantity of free hydrocarbon-containing compounds contained in a sedimentary rock, by distinguishing them from the hydrocarbon-containing compounds retained in the organic matter of the sedimentary rock.

The present invention can be applied to any type of sedimentary rock, such as for example to a source rock, a reservoir rock or an unconventional source rock.

The method according to the invention requires the following to be available:
- at least one representative sample of the sedimentary rock being studied: which can have been taken by core boring or from debris originating from drilling. Advantageously, the sample as taken is prepared (by washing, sieving, sorting etc.) in order to eliminate the impurities (drilling mud, for example, pollutants etc.) therefrom;
- at least one representative sample of the isolated total organic matter originating from the sedimentary rock being studied which can advantageously be obtained from a part of the sample of sedimentary rock as described above, from which the mineral fraction is eliminated by a procedure of hot acid attack and drying of samples, as described for example in the document (Durand and Nicaise, 1980). Advantageously, the representative sample of the isolated total organic matter originates from the same interval of sedimentary rock as the representative sample of the sedimentary rock studied.

The method according to the invention can advantageously, but not in a limiting manner, be implemented by use of the ROCK-EVAL® device (IFP Energies nouvelles, France), as described in the patents FR 2227797 which corresponds to U.S. Pat. No. 3,953,171 and FR 2472754 which corresponds to U.S. Pat. No. 4,352,673. In fact, the ROCK-EVAL® device comprises at least:
- a pyrolysis furnace under a non-oxidizing atmosphere,
- means for transferring pyrolysis residues into an oxidation furnace,
- an oxidation furnace under oxidizing atmosphere,
- means for measuring the quantity of hydrocarbon-containing compounds released during pyrolysis,
- means for measuring carbon monoxide (CO) and carbon dioxide ($CO_2$).

The method of the invention can also be implemented by a single pyrolysis furnace, capable of operating under a non-oxidizing atmosphere and under an oxidizing atmosphere, which cooperates with a device for measuring the quantity of hydrocarbon-containing compounds released during pyrolysis, and a device for measuring carbon monoxide and carbon dioxide.

The method according to the invention comprises at least the following steps:

1—Heating sequence under an inert atmosphere (pyrolysis)

2—Heating sequence under an oxidizing atmosphere (oxidation)

3—Quantification of the free hydrocarbons

The first two steps are each applied to at least one representative sample of the sedimentary rock (also called sample of sedimentary rock below) being studied and to a representative sample of the isolated total organic matter contained in the sedimentary rock being studied (called sample of organic matter below). It is possible for example to apply the first step to the sample of sedimentary rock, repeat (or apply in parallel) this first step for the sample of organic matter, apply the second step to the residue of the sample of sedimentary rock obtained after the heating sequence under an inert atmosphere, and finally apply (or apply in parallel) the second step to the residue of the sample of organic matter obtained after the heating sequence under an oxidizing atmosphere.

The steps of the method according to the invention are detailed below.

1. Heating Sequence Under an Inert Atmosphere (Pyrolysis)

During this step, a given sample, either of sedimentary rock or organic matter, is heated under an inert atmosphere (such as for example under a flow of nitrogen, helium) according to a predefined sequence of temperatures that are variable over time.

According to an implementation of the invention, it is possible for example to do this using the sequence of temperatures given in patent EP 0691540 B1 which corresponds to U.S. Pat. No. 5,843,787.

According to a preferred implementation of the invention, the program of temperatures implemented for the first step of the invention is suitable for completely releasing the hydrocarbon-containing compounds of low molecular weight from the sample in question.

Advantageously, the program of temperatures implemented for the first step of the invention is also suitable for separately releasing the hydrocarbon-containing compounds of low and high molecular weight. Such a sequence of temperatures is for example defined in the application FR 3021749 which corresponds to US published patent application 2015/0346179. According to this very preferred implementation of the invention, the following heating sequence under an inert atmosphere is applied to a given sample:

a) starting from a first temperature value (T1) between 50° C. and 120° C., raising the temperature of the sample according to a first temperature gradient between 1° C./min and 50° C./min, up to a second temperature value (T2) between 180° C. and 220° C., and maintaining the sample at the second temperature value (T2) during a first predetermined duration;

b) starting from the second temperature value (T2), raising the temperature of said sample according to a second temperature gradient between 1° C./min and 50° C./min, up to a third temperature value (T3) between 330° C. and 370° C., and maintaining the sample at said third temperature value (T3) during a second predetermined duration; and c) starting from the third temperature value (T3), raising the temperature of the sample according to a third temperature gradient between 1° C./min and 50° C./min, up to a fourth temperature value (T4) between 630° C. and 670° C.

Thus, this very preferred sequence of temperatures contains a succession of three heating steps, separated by two temperature maintenance steps. Such a sequence is particularly well suited to releasing all of the hydrocarbon-containing compounds present in a sample, that is hydrocarbon-containing compounds from low, high to very high molecular weight, the light hydrocarbon-containing compounds furthermore being released completely and separately from the heavy compounds. In fact, the preliminary step of maintaining the sample at the first temperature (T1) allows the release of very light hydrocarbon-containing compounds present in a sample. Moreover, the second temperature (T2) corresponds substantially with the end of the phase of thermovaporization of the lightest hydrocarbons contained in the sample, and with the start of the phase of pyrolytic cracking of the heavy compounds. The third temperature (T3) corresponds substantially with the end of the phase of thermovaporization of the heavy hydrocarbons contained in the sample, and with the start of the phase of pyrolytic cracking of the very heavy compounds (kerogen, NSO). The fourth temperature (T4) corresponds substantially to the end of the thermal cracking of the organic matter present in the sample.

According to a mode of implementation of the present invention, the sample is maintained at the first temperature (T1) for a non-zero duration, for example comprised between 2 and 6 minutes. This preliminary step of maintaining the sample at the first temperature (T1) makes possible to at least one of bringing the sample up to temperature and releasing the very light hydrocarbon-containing compounds present in a sample that is damaged only slightly or not at all.

According to an implementation of the invention, the sample is maintained at the second temperature (T2) for a first predetermined non-zero duration, for example greater than half a minute and preferentially between 2 and 4 minutes.

According to an implementation of the invention, the third temperature (T3) is maintained for a second predetermined non-zero duration, for example greater than half a minute and preferentially between 2 and 4 minutes.

According to an implementation of the invention, the value of the fourth temperature (T4) is between 630° C. and 670° C., preferentially between 640° C. and 660° C. The temperature gradient is advantageously between 20° C./minute and 30° C./minute.

According to a preferential embodiment, at least one of the first, the second, and the third temperature gradient is between 20° C./minute and 30° C./minute.

According to the invention, the representative quantity of the hydrocarbon-containing compounds released during at least a part of the heating under an inert atmosphere and while the quantity of $CO_2$ and of CO contained in the effluent resulting from the heating are also continuously measured. In other words, at the end of this step being applied to a given sample, a first curve representative of the quantity of hydrocarbon-containing compounds released over time during at least one part of the pyrolysis phase is obtained, as well as a second curve representative of the quantity of CO and $CO_2$ released over time during the pyrolysis phase. Measurement of the quantity of hydrocarbon-containing compounds can be carried out by use of a detector of the flame ionization (FID) type. Measurement of the quantity of CO and $CO_2$ released can be carried out by use of a detector of the infrared (IR) type.

Figure 2:
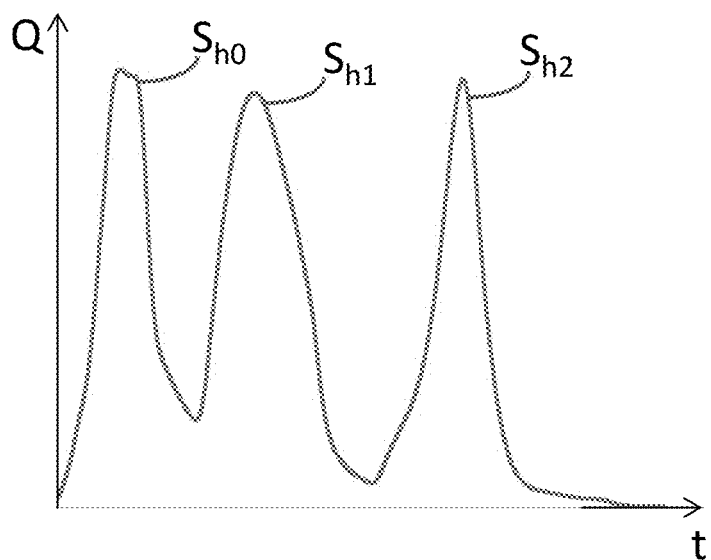
FIG. 2 shows the change of the quantity of hydrocarbon-containing compounds (Q) over time (t) during a pyrolysis carried out on a given sample, according to the heating sequence under an inert atmosphere in FIG. 1.
Figure 3:
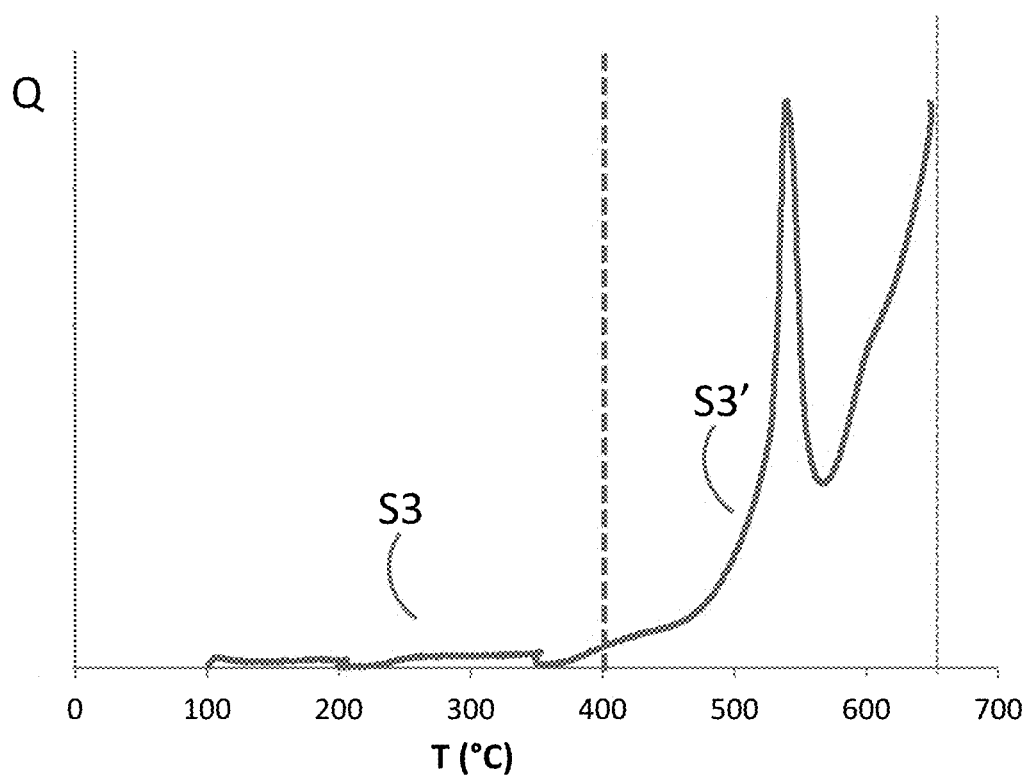
FIG. 3 shows the change in the quantity (Q) of $CO_2$ generated as a function of the temperature (T) during a pyrolysis carried out on a given sample, according to the heating sequence under an inert atmosphere in FIG. 1.
Figure 4:
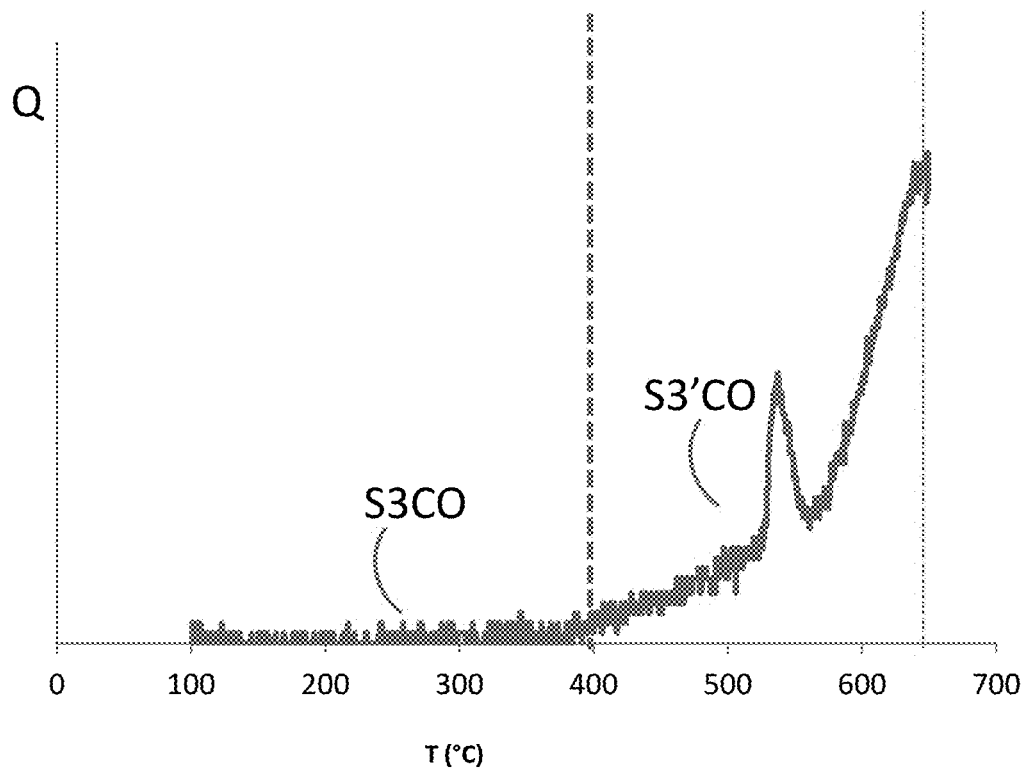
FIG. 4 shows the change in the quantity (Q) of CO generated as a function of the temperature (T) during a pyrolysis carried out on a given sample, according to the heating sequence under an inert atmosphere in FIG. 1.

An example of curves measured during this first step for a given sample are shown in FIG. 2 (described above), in FIG. 3 and in FIG. 4. FIG. 2 (described above) shows the quantity of hydrocarbon-containing compounds released during heating under an inert atmosphere. This curve shows the three peaks $S_{h0}$, $S_{h1}$ and $S_{h2}$ described above. The curve in FIG. 3 shows the quantity of $CO_2$ contained in the effluent resulting from heating under an inert atmosphere. Conventionally, two zones (delimited by a dotted line on FIG. 3, to the right and to the left of a temperature substantially equal to 400° C.), a first zone, denoted S3, corresponding to the $CO_2$ generated by cracking the organic matter of the sample in question during heating under an inert atmosphere, and a zone S3' which corresponds to the $CO_2$ generated by cracking of the mineral matrix during heating under an inert atmosphere. The curve in FIG. 4 shows the quantity of CO contained in the effluent resulting from heating under an inert atmosphere. Conventionally, based on this recording, two zones (delimited by a dotted line on FIG. 4, to the right and to the left of a temperature substantially equal to 400° C.), a first zone, denoted S3CO, corresponding to the CO generated by cracking the organic matter of the sample in question during heating under an inert atmosphere, and a zone S3'CO corresponding to the CO generated by cracking of the mineral matrix during heating under an inert atmosphere.

According to the invention, this step is applied to each of the samples necessary for implementing the invention, that is at least to the sample of sedimentary rock in question and to the sample of organic matter corresponding to this sample of sedimentary rock. Advantageously, the same sequence of temperatures is applied under an inert atmosphere to each of the samples.

2. Heating Sequence Under an Oxidizing Atmosphere (Oxidation)

During this second step, the solid residue from one of the samples obtained at the end of the pyrolysis sequence as described in step 1 above is subjected to oxidation according to a predefined program of temperatures that are variable over time.

The program of temperatures of the heating sequence under an oxidizing atmosphere can for example be in the following form: starting from a temperature between 200° C. and 400° C., and preferably the value 300° C., the temperature of the residue of the sample in question is raised according to a temperature gradient between 20 and 40° C./minute, up to an end of oxidation temperature between 750 and 950° C., and preferably the value 850° C.

According to the invention, a representative quantity of CO and $CO_2$ released during this second heating sequence is continuously measured. According to an implementation of the invention, this measurement can be carried out by a detector of the infrared (IR) type.

Figure 5:
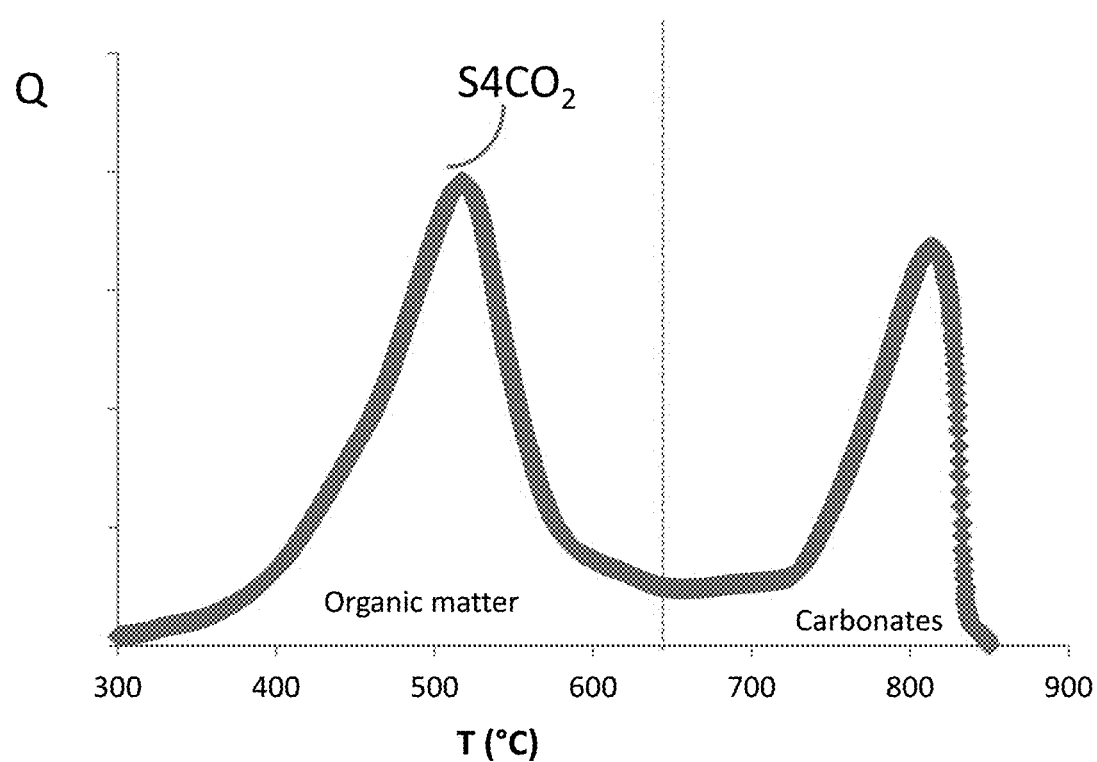
FIG. 5 shows the change in the quantity (Q) of $CO_2$ generated as a function of the temperature (T) during the oxidation cycle at the end of the pyrolysis sequence on a given sample.
Figure 6:
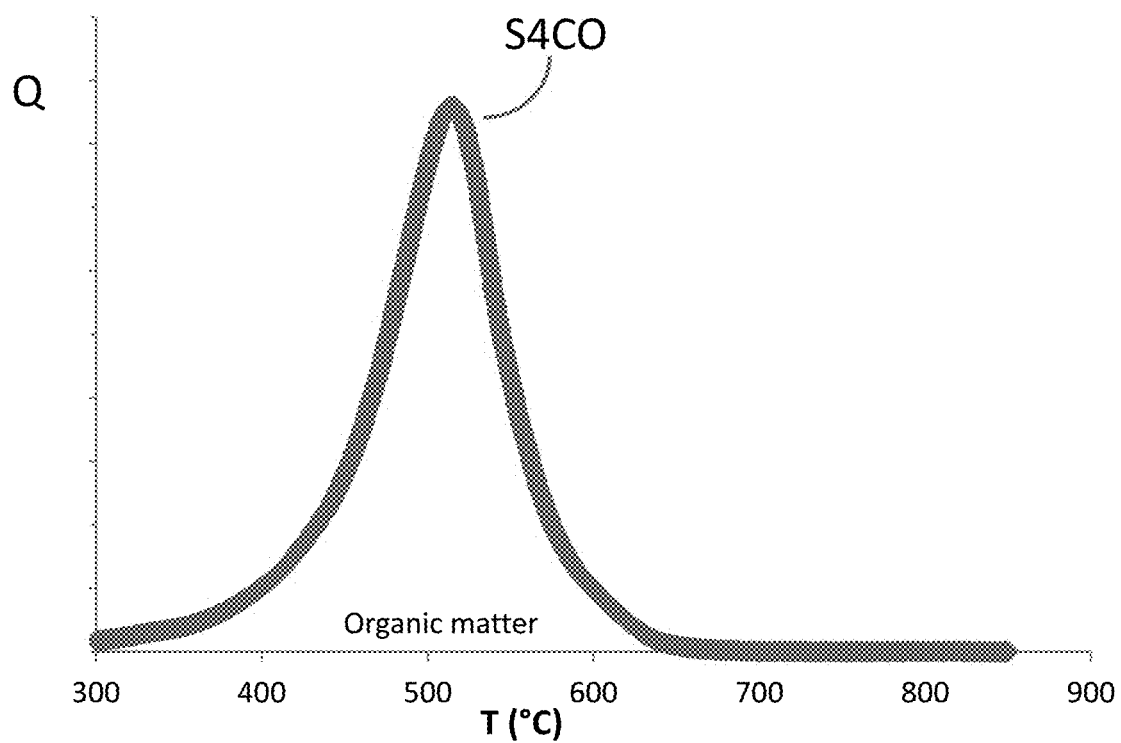
FIG. 6 shows the change in the quantity (Q) of CO generated as a function of the temperature (T) during the oxidation cycle at the end of the pyrolysis sequence on a given sample.

An example of curves measured during this step is shown in FIG. 5 and in FIG. 6. The curve in FIG. 5 (respectively FIG. 6) represents the quantity of $CO_2$ (respectively CO) contained in the effluent resulting from heating the pyrolysis residue under an oxidizing atmosphere. In particular, in FIG. 5 (respectively FIG. 6) the presence of the peak S4CO2 (respectively S4CO) which corresponds to the quantity of $CO_2$ (respectively CO) generated by cracking the organic matter during the oxidation cycle can be observed.

According to the invention, this step is applied to each of the pyrolysis residues of the samples necessary for implementing the invention, that is at least to the pyrolysis residue of the sample of sedimentary rock in question and to the pyrolysis residue of the sample of organic matter corresponding to this sample of sedimentary rock. Advantageously, the same sequence of temperatures is applied under an oxidizing atmosphere to each of the residues.

3. Quantification of the Free Hydrocarbons

At the end of the two preceding steps, each applied to a sample of sedimentary rock and to a sample of organic matter corresponding to the sample of sedimentary rock, measurements of the quantity of hydrocarbon-containing compounds and measurements of the CO and $CO_2$ released by each of the samples are available, that is at least the sample of sedimentary rock and the corresponding sample of organic matter.

According to the invention, the parameter representative of the quantity of hydrocarbon-containing compounds present in free form within the sedimentary rock being studied is determined from at least measurements of the quantity of hydrocarbon-containing compounds, as well as quantities of CO and $CO_2$ released by each of the samples, that is at least the sample of sedimentary rock and the corresponding sample of organic matter.

According to an implementation of the invention, the parameter $HC_{Free}$ representative of the quantity of hydrocarbon-containing compounds present in free form within the sedimentary rock is determined from the difference between a parameter $HC_{Total,rock}$ representative of the quantity of hydrocarbon-containing compounds present in a free and retained form in the rock sample and at least the parameter $HC_{Sorbed,TOM}$ representative of the quantity of hydrocarbon-containing compounds present in retained form in the sample of organic matter with the parameters $HC_{Total,rock}$ and $HC_{Sorbed,TOM}$ being determined at least from the measurements described in steps 1 and 2.

According to an implementation of the invention, the parameter $HC_{Total,rock}$ representative of the quantity of hydrocarbon-containing compounds, both free and retained, in the rock sample are determined from at least the representative quantity of hydrocarbon-containing compounds released during at least a part of the heating sequence under an inert atmosphere applied to the rock sample and from the level of total organic carbon $TOC_{rock}$ determined for the rock sample.

According to an implementation of the invention, the parameter $HC_{Sorbed,TOM}$ representative of a quantity of hydrocarbon-containing compounds present in retained form in the sample of organic matter corresponding to the sample of sedimentary rock being studied is determined from at least the quantity of hydrocarbon-containing compounds released during at least a part of the heating sequence under an inert atmosphere applied to the sample of organic matter and from the level of total organic carbon $TOC_{TOM}$ of the sample of organic matter.

According to an implementation of the invention, the parameter $HC_{Total,rock}$ representative of the quantity of hydrocarbon-containing compounds both free and retained in the rock sample is determined according to a formula of the type:

$$HC_{Total,rock} = \frac{SurfQ_{rock}}{m_{rock} * TOC_{rock}},$$

where $SurfQ_{rock}$ corresponds to at least a part of the area under the measurement curve of the quantity of hydrocarbon-containing compounds released by the rock sample, and $m_{rock}$ corresponds to the initial mass, before pyrolysis, of the sample of sedimentary rock. According to an implementation of the invention, $SurfQ_{rock}$ can for example correspond to the area under the measurement curve of the quantity of hydrocarbon-containing compounds released by the rock sample between the two predetermined temperatures of the heating sequence under an inert atmosphere, for example so as to target more specifically hydrocarbon-containing compounds of a molecular weight of interest to the user of the invention.

According to an implementation of the invention according to which the heating sequence under an inert atmosphere is the very preferred sequence as described in step 1 above, at least the following is determined:

a parameter $HC_{Total,rock}^{Sh0}$ representative of the quantity of light thermovaporizable hydrocarbon-containing compounds (the number of carbon atoms of which is less than approximately 20) both free and retained in the sample of sedimentary rock according to a formula of the type:

$$HC_{Total,rock}^{Sh0} = \frac{SurfSh0_{rock}}{m_{rock} * TOC_{rock}},$$

and/or a parameter $HC_{Total,rock}^{Sh1}$ representative of the quantity of heavy thermovaporizable hydrocarbon-containing compounds (the number of carbon atoms of which is substantially comprised between 20 and 30) both free and retained in the sample of sedimentary rock according to a formula of the type:

$$HC_{Total,rock}^{Sh1} = \frac{SurfSh1_{rock}}{m_{rock} * TOC_{rock}},$$

and/or a parameter $HC_{Total,rock}^{Sh0+Sh1}$ representative of the quantity of light to heavy thermovaporizable hydrocarbon-containing compounds (the number of carbon atoms of which is less than approximately 30) both free and retained in the sample of sedimentary rock according to a formula of the type:

$$HC_{Total,rock}^{Sh1} = \frac{SurfSh1_{rock}}{m_{rock} * TOC_{rock}},$$

where $SurfSh0_{rock}$ and $SurfSh1_{rock}$ correspond respectively to the area under the peaks $S_{h0}$ and $S_{h1}$ of the measurement curve of the hydrocarbon-containing compounds released during the heating sequence by pyrolysis applied to the sample of sedimentary rock, given in my;

$m_{rock}$ corresponds to the initial mass, before pyrolysis, of the sample of sedimentary rock, in mg;

$TOC_{rock}$ corresponds to the total organic carbon content of the sample of sedimentary rock, in wt %.

According to an implementation of the invention, the parameter $HC_{Sorbed,TOM}$ representative of the quantity of hydrocarbon-containing compounds retained in the sample of organic matter is determined according to a formula of the type:

$$HC_{Sorbed,TOM} = \frac{SurfQ_{TOM}}{m_{TOM} * TOC_{TOM}},$$

where $SurfQ_{TOM}$ corresponds to at least a part of the area under the measurement curve of the quantity of hydrocarbon-containing compounds released by the sample of organic matter, and $m_{TOM}$ corresponds to the initial mass, before pyrolysis, of the sample of organic matter. According to an implementation of the invention, $SurfQ_{TOM}$ can for example correspond to the area under the measurement curve of the quantity of hydrocarbon-containing compounds released by the sample of organic matter between two predetermined temperatures of the heating sequence under an inert atmosphere, for example so as to target more specifically hydrocarbon-containing compounds of a molecular weight of interest to the user of the invention. Advantageously, the range of temperatures between which the quantities $SurfQ_{TOM}$ and $SurfQ_{rock}$ which are calculated are identical.

According to an implementation variant of the invention according to which the heating sequence under an inert atmosphere is the very preferred sequence as described in step 1 above, at least the following is determined:

a parameter $HC_{Sorbed,TOM}^{Sh0}$ representative of the quantity of light thermovaporizable hydrocarbon-containing compounds (the number of carbon atoms of which is less than approximately 20) retained in the sample of organic matter, defined according to a formula of the type:

$$HC_{Sorbed,TOM}^{Sh0} = \frac{SurfSh0_{TOM}}{m_{TOM} * TOC_{TOM}},$$

and/or
a parameter $HC_{Sorbed,TOM}^{Sh1}$ representative of the quantity of heavy thermovaporizable hydrocarbon-containing compounds (the number of carbon atoms of which is substantially comprised between 20 and 30) retained in the sample of organic matter, defined according to a formula of the type:

$$HC_{Sorbed,TOM}^{Sh1} = \frac{SurfSh1_{TOM}}{m_{TOM} * TOC_{TOM}},$$

and/or
a parameter $HC_{Sorbed,rock}^{Sh0+Sh1}$ representative of the quantity of light to heavy thermovaporizable hydrocarbon-containing compounds (the number of carbon atoms of which is less than approximately 30) retained in the sample of sedimentary rock, defined according to a formula of the type:

$$HC_{Sorbed,TOM}^{Sh0+Sh1} = \frac{SurfSh0_{TOM} + SurfSh1_{TOM}}{m_{TOM} * TOC_{TOM}},$$

where:
$SurfSh0_{TOM}$ and $SurfSh1_{TOM}$ correspond respectively to the area under the peaks $S_{h0}$ and $S_{h1}$ of the measurement curve of the hydrocarbon-containing compounds released during the heating sequence by pyrolysis applied to the sample of organic matter, and are given in mV;

$m_{TOM}$ corresponds to the initial mass, before pyrolysis, of the sample of organic matter, in mg;
$TOC_{TOM}$ corresponds to the total organic carbon content of the sample of organic matter, in wt %.

According to an implementation of the invention, the parameters $TOC_{rock}$ and $TOC_{TOM}$, which correspond respectively to the total organic carbon content of the sample of sedimentary rock and the corresponding sample of organic matter, are determined from the measurement curves of CO and $CO_2$ resulting from heating sequences under an inert atmosphere (cf step 1 above) and under an oxidizing atmosphere (cf. step 2 above). These curves are established both for the sample of sedimentary rock and for the sample of organic matter (repetition of steps 1 and 2 for each of the samples).

Generally, the total organic carbon content of a rock sample can be obtained according to a formula of the type:

$$TOC_{rock}(wt\%) = PC(wt\%) + RC(wt\%)$$

where PC corresponds to the pyrolyzed carbon and RC corresponds to the residual carbon. The document (Behar et al, 2001), gives a method for calculating the TOC in the case of a rock sample. According to an implementation of the invention according to which the heating sequence under an inert atmosphere is the very preferred sequence as described in step 1 above, the pyrolyzed carbon PC and the residual carbon RC are determined according to the following formulae:

$$PC (wt\%) = \frac{[(SurfSh0 + SurfSh1 + SurfSh2)*0.083] + \left[SurfS3 * \frac{12}{44}\right] + \left[SurfS3CO + \frac{SurfS3'CO}{2}\right) * \frac{12}{18}}{10}, \text{ and}$$

$$RC (wt\%) = \left(SurfS4CO_2 * \frac{12}{440}\right) + \left(SurfS4CO * \frac{12}{280}\right).$$

The document (Behar et al, 2001), also gives a method for calculating the TOC in the case of a sample of organic matter. According to an implementation of the invention according to which the heating sequence under an inert atmosphere is the very preferred sequence as described in step 1 above, the total organic carbon content of a sample of organic matter can be obtained according to a formula of the type:

$$TOC_{TOM}(wt\%) = \frac{\begin{bmatrix} (0.83 * (SurfSh0 + SurfSh1 + SurfSh2) + \\ \left(\frac{12}{44} * (SurfS3 + SurfS3' + SurfS4CO_2)\right) + \\ \left(\frac{12}{28} * (SurfS3CO + SurfS3'CO + SurfS4CO)\right) \end{bmatrix}}{10}$$

where
SurfSh0 corresponds to the area under the peak Sh0 described above corresponding to the light thermovaporizable hydrocarbons, SurfSh1 corresponds to the area under the peak Sh1 described above corresponding to the heavy thermovaporizable hydrocarbons, and SurfSh2 corresponds to the area under the peak Sh2 described above corresponding to the very heavy thermovaporizable hydrocarbons and to the hydrocarbons originating from the thermal cracking of kerogen which are given in mV;

SurfS3 corresponds to the area under the zone S3 described above corresponding to the quantity of $CO_2$ generated by cracking the organic matter during heating under an inert atmosphere, and SurfS3' corresponds to the area under the zone S3' described above corresponding to the quantity of $CO_2$ generated by cracking the mineral matrix during heating under an inert atmosphere which are given in mV;

SurfS4CO2 corresponds to the area under the peak S4CO2 described above corresponding to the quantity of $CO_2$ generated by cracking the organic matter during the oxidation cycle, and SurfS4CO corresponds to the area under the peak S4CO described above corresponding to the quantity of CO generated by cracking the organic matter during the oxidation cycle which are given in mV;

SurfS3CO corresponds to the area under the peak S3CO described above corresponding to the quantity of CO generated by cracking the organic matter during the pyrolysis cycle, and SurfS3'CO corresponds to the area under the peak S3'CO described above corresponding to the quantity of CO generated by cracking the mineral matrix during the pyrolysis cycle which are given in mV.

According to an implementation of the invention, the parameter $HC_{Free}$ representative of the quantity of hydrocarbon-containing compounds present in free form in the rock is determined according to the following formula:

$$HC_{Free} = HC_{Total,rock} - HC_{Sorbed,TOM}.$$

According to an implementation of the invention according to which the heating sequence under an inert atmosphere is the very preferred sequence as described in step 1 above, at least one parameter $HC_{Free}^{Shx}$ representative of the quantity of light and/or heavy hydrocarbon-containing compounds free in the sedimentary rock is determined according to a formula of the type:

$$HC_{Free}^{Shx} = HC_{Total,rock}^{Shx} - HC_{Sorbed,TOM}^{Shx}, \text{ with Shx}$$
selected from {Sh0, Sh1, Sh0+Sh1}.

According to an implementation of the invention, at least one parameter representative of the proportion of free hydrocarbon-containing compounds is determined with respect to the retained hydrocarbon-containing compounds.

According to an implementation of the invention according to which the heating sequence under an inert atmosphere is the very preferred sequence as described in step 1 above, the following is determined:

a parameter representative of the proportion of free light hydrocarbon-containing compounds in the sample of sedimentary rock with respect to the light hydrocarbon-containing compounds, both free and retained, in the sample of sedimentary rock according to a formula of the type:

$$\% HC_{Free}^{Sh0} = HC_{Free}^{Sh0} / HC_{Total,rock}^{Sh0} * 100, \text{ and/or}$$

a parameter representative of the proportion of light hydrocarbon-containing compounds retained in the sample of sedimentary rock with respect to the light hydrocarbon-containing compounds, both free and retained, in the sample of sedimentary rock according to a formula of the type:

$$\% HC_{Sorbed}^{Sh0} = HC_{Sorbed,TOM}^{Sh0} / HC_{Total,rock}^{Sh0} * 100,$$
and/or a parameter representative of the proportion of free light and heavy hydrocarbon-containing compounds in the sample of sedimentary rock, with respect to the light and heavy hydrocarbon-containing compounds, both free and retained, in the sample of sedimentary rock according to a formula of the type:

$$\% HC_{Free}^{Sh0+Sh1} = HC_{Free}^{Sh0+Sh1} / HC_{Total,rock}^{Sh0+Sh1} * 100, \text{ and/or}$$

a parameter representative of the proportion of light and heavy hydrocarbon-containing compounds retained in the sample of sedimentary rock, with respect to the light and heavy hydrocarbon-containing compounds, both free and retained, in the sample of sedimentary rock according to a formula of the type:

$$\% HC_{Sorbed}^{Sh0+Sh1} = HC_{Sorbed,TOM}^{Sh0+Sh1} / HC_{Total,rock}^{Sh0+Sh1} * 100.$$

The proportion parameters as defined above are simplified indicators that can contribute to estimating the oil potential of the sedimentary rock from which the samples analyzed in the above-described steps 1 and 2 originate.

Examples of Applications

The method according to the invention has been applied based on four samples (respectively E1, E2, E3 and E4) of a sedimentary rock, taken at different depths (respectively 3094 m, 3099 m, 3106 and 3112 m) in a well. The sedimentary rock being studied is a marine clay from the Jurassic period, from the Vaca Muerta Formation of the Néuquen sedimentary basin in Argentina. These samples were preserved in resins then prepared (by washing, sieving, sorting etc.) in order to eliminate the impurities (drilling mud for example, pollutants etc.) therefrom.

From each of these samples, four representative samples of the isolated total organic matter were extracted from each sample according to the invention by proceeding in the following manner: from a part of each sample of sedimentary rock, the mineral fraction was eliminated by conventional acid attack and heat drying. Thus, four pairs of samples are formed with each pair comprising a representative sample of the sedimentary rock and a representative sample of the isolated total organic matter from this rock sample.

Then the steps of the method according to the invention as described above were applied to each of the samples of sedimentary rock and their corresponding sample of organic matter. In order to do this, the very preferred heating sequence under an inert atmosphere, described in step 1, was used in particular.

Figure 7:
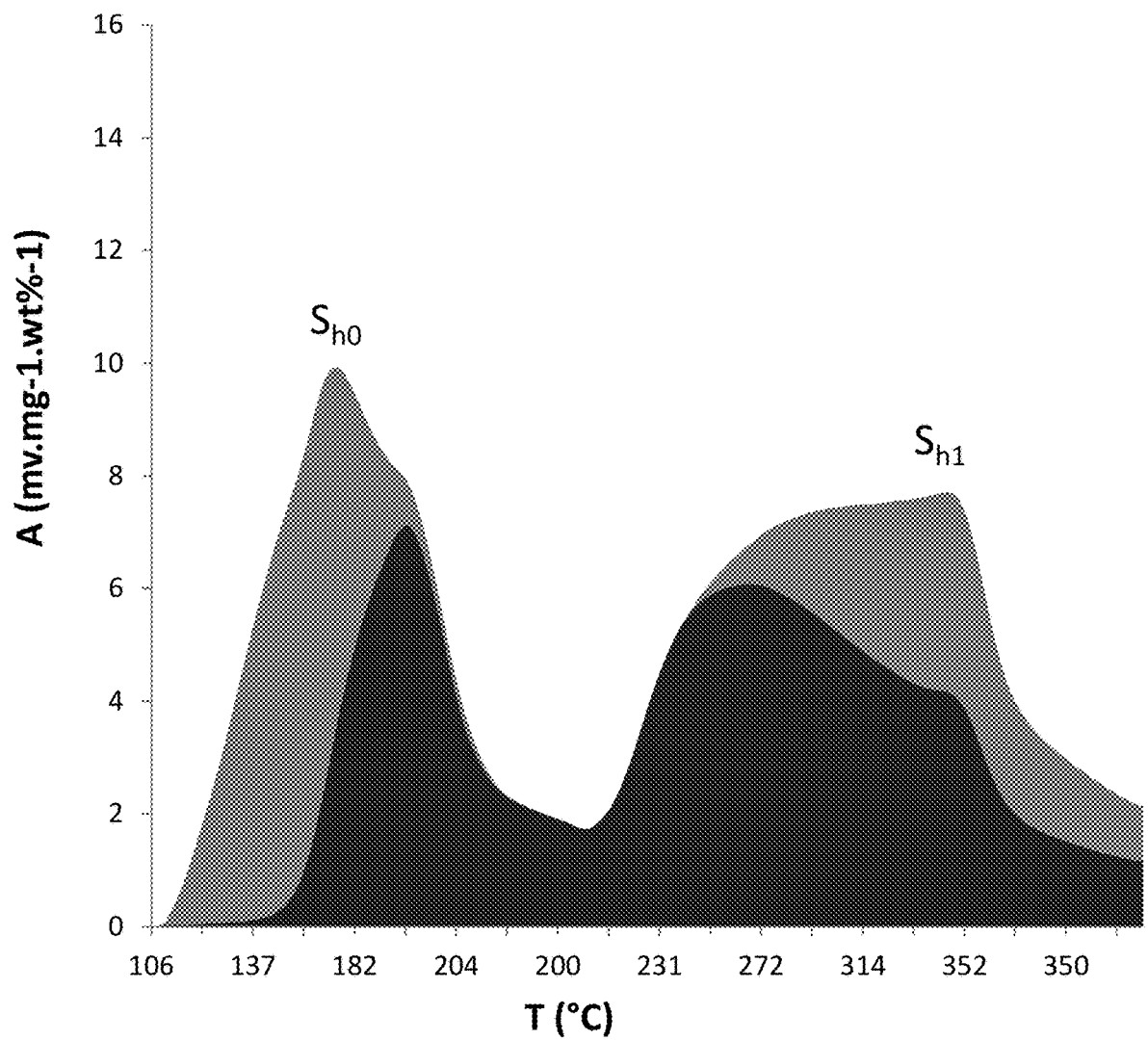
FIG. 7 shows the change in the quantity of free and retained hydrocarbon-containing compounds released as a function of the temperature T of a heating sequence as described in FIG. 1, for a pair of source rock-organic matrix samples according to the invention.

FIG. 7 shows the change in the amplitude A (normalized by the initial mass and the TOC of the sample analyzed) measured by a flame ionization detector during the heating sequence under an inert atmosphere, between the temperatures (T) comprised between 100° C. and 370° C. for the requirements of this representation, of the rock sample E4 (curve delimited by the upper edge of the surface area marked in dark grey) and of the corresponding sample of isolated total organic matter (curve delimited by the surface area marked in dark grey and the surface area marked in black). In this figure, the presence of the two peaks representative of the quantity of light (peak Sh0) and heavy (peak Sh1) hydrocarbon-containing compounds released can be seen in particular. By way of illustration, this figure also shows the part of each of the two peaks corresponding to the free hydrocarbon-containing compounds (part of each of the peaks in dark grey) and to the retained hydrocarbon-containing compounds (part of each of the peaks in black). Moreover, the total organic carbon contents for the sample of sedimentary rock and for the corresponding sample of organic matter is determined i.e.: $TOC_{rock}$=4.9 wt % and $TOC_{TOM}$=49.1 wt %.

According to the invention, for this pair of samples associated with the sample of sedimentary rock E4, the quantity of light and/or heavy hydrocarbon-containing compounds in the sedimentary rock is determined, i.e.:

$HC_{Free}^{Sh0}$=1004 mV·mg$^{-1}$·wt %$^{-1}$;
$HC_{Free}^{Sh1}$=822 mV·mg$^{-1}$·wt %$^{-1}$;
$HC_{Free}^{Sh0+Sh1}$=1826 mV·mg$^{-1}$·wt %$^{-1}$;

In addition, the values of the parameters % $HC_{Free}^{Sh0}$, % $HC_{Sorbed}^{Sh0}$, % $HC_{Free}^{Sh0+Sh1}$ and % $HC_{Sorbed}^{Sh0+Sh1}$ representative of the proportion of free hydrocarbon-containing compounds with respect to the retained hydrocarbon-containing compounds as described in step 3 are determined, for the sample E4, i.e.:

% $HC_{Free}^{Sh0}$=48%,
% $HC_{Sorbed}^{Sh0}$=52%
% $HC_{Free}^{Sh0+Sh1}$=37%,
% $HC_{Sorbed}^{Sh0+Sh1}$=63%.

Figure 8A:
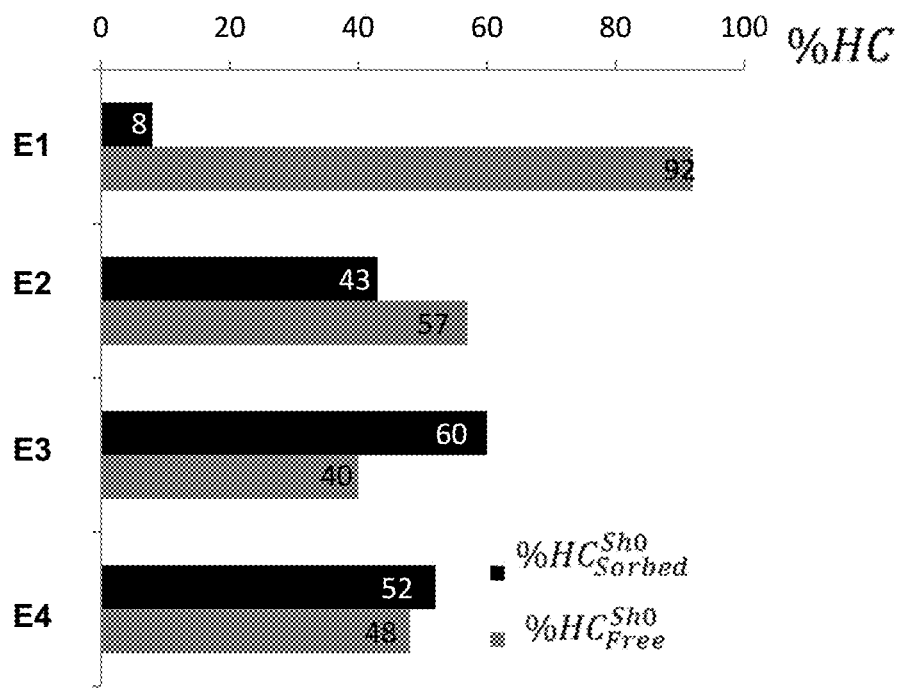
FIGS. 8A and 8B represent parameters representative of the proportion between free and retained hydrocarbon-containing compounds, determined for four pairs of source rock-organic matrix samples according to the invention.
Figure 8B:
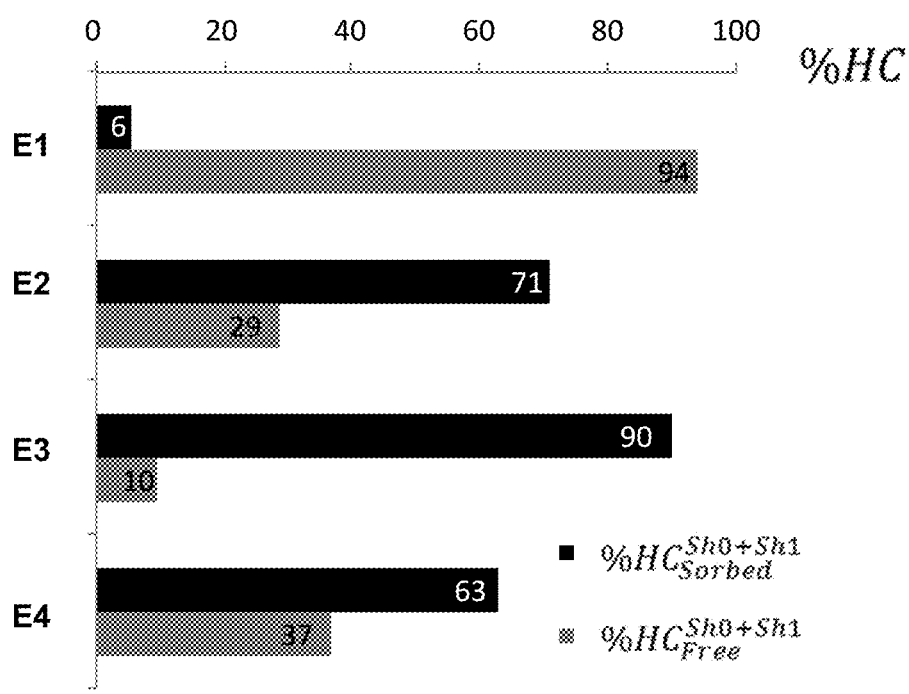

FIG. 8A (respectively FIG. 8B) shows the values of the parameters % $HC_{Free}^{Sh0}$ and % $HC_{Sorbed}^{Sh0}$ (respectively % $HC_{Free}^{Sh0+Sh1}$ and % $HC_{Sorbed}^{Sh0+Sh1}$) representative of the proportion of free hydrocarbon-containing compounds with respect to the retained hydrocarbon-containing compounds as described in step 3 for each of the four samples E1, E2, E3 and E4.

It can thus be concluded that the deepest sedimentary rock interval (E4) is mainly dominated by approximately 60% hydrocarbons retained in the organic matter, while the shallower sample (E1) contains more than 90% free hydrocarbons.

Such information is of great interest for estimating the oil potential of the sedimentary rock from which the rock samples analyzed by the method according to the invention originate, since, by separating the retained hydrocarbon-containing compounds from the free hydrocarbon-containing compounds among the light and/or heavy hydrocarbon-containing compounds, the method according to the invention allows for a more accurate estimate of the quantity of hydrocarbons that can actually be recovered.

The invention claimed is:

1. A method for determining a parameter representative of a quantity of hydrocarbon-containing compounds present in free form within a sedimentary rock, wherein a first sample representative of the sedimentary rock is obtained and a second sample which is representative of an isolated total organic matter in the sedimentary rock is obtained by eliminating a free mineral part of the sedimentary rock, with each of the samples being processed according to steps comprising:

A. heating the sample according to a first heating sequence under an inert atmosphere, and continuously measuring a representative quantity of the hydrocarbon-containing compounds released during at least a part of the first heating sequence and a representative quantity of CO and a representative quantity of $CO_2$ released during the first heating sequence; and B. heating a residue of the sample originating from the first heating sequence according to a second heating sequence under an oxidizing atmosphere, and measuring a representative quantity of CO and a representative quantity of $CO_2$ released during the second heating sequence; and determining the parameter representative of the quantity of hydrocarbon-containing compounds present in free form within the sedimentary rock from at least measurements obtained from the first and second samples.

2. The method according to claim 1, comprising at an end of steps A and B applied at least to the first and to the second samples:

i. determining for each of the samples, a level of total organic carbon from the measurements of the quantity of $CO_2$ and CO, obtained during the first and second heating sequences;

ii. determining a parameter representative of a quantity of hydrocarbon-containing compounds present in the first sample in both a free and retained form, from at least the measurement of the representative quantity of the hydrocarbon-containing compounds released during the part of the first heating sequence applied to the first sample, and from the level of total organic carbon determined in the first sample;

iii. determining a parameter representative of a quantity of hydrocarbon-containing compounds present in the second sample in retained form, from at least the measurement of the representative quantity of the hydrocarbon-containing compounds released during the part of the first heating sequence applied to the second sample and the level of total organic carbon determined in the second sample; and determining the parameter representative of the quantity of hydrocarbon-containing compounds present in free form in the sedimentary rock from a difference between the parameter representative of the quantity of hydrocarbon-containing compounds present in the first sample in both a free and in a retained form and at least the parameter representative of the quantity of hydrocarbon-containing compounds present in the second sample in retained form.

3. The method according to claim 2, wherein the heating sequence in step B starts from a temperature between 200° C. and 400° C., and is raised according to a temperature gradient comprised between 20 and 40° C./minute, up to a temperature between 750 and 950° C.

4. The method according to claim 3, comprising determining the parameter representative of the quantity of hydrocarbon-containing compounds present in the first sample in both a free and a retained form by solving a formula:

$$HC_{Total,rock} = \frac{SurfQ_{rock}}{m_{rock} * TOC_{rock}}$$

wherein $SurfQ_{rock}$ corresponds to at least a part of an area under the measurement curve of the quantity of hydrocarbon-containing compounds released by the first sample, $m_{rock}$ which is an initial mass of the first sample, and $TOC_{rock}$ is the level of total organic carbon determined in the first sample.

5. The method according to claim 4, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein SurfQ$_{TOM}$ corresponds to at least a part of an area under the measurement curve of the quantity of hydrocarbon-containing compounds released by the second sample, m$_{TOM}$ which is an initial mass of the second sample, and TOC$_{TOM}$ is a level of total organic carbon determined for the second sample.

6. The method according to claim 3, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein SurfQ$_{TOM}$ corresponds to at least a part of an area under the measurement curve of the quantity of hydrocarbon-containing compounds released by the second sample, m$_{TOM}$ which is an initial mass of the second sample, and TOC$_{TOM}$ is a level of total organic carbon determined for the second sample.

7. The method according to claim 3, comprising performing step A by heating a selected sample from the first sample and the second sample under an inert atmosphere comprising:
 a) starting heating from a first temperature between 50° C. and 120° C., raising the temperature of the selected sample according to a first temperature gradient between 1° C./min and 50° C./min, up to a second temperature between 180° C. and 220° C., and maintaining the selected sample at the second temperature for a first predetermined duration;
 b) starting heating from the second temperature, raising the temperature of the selected sample according to a second temperature gradient between 1° C./min and 50° C./min, up to a third temperature between 330° C. and 370° C., and maintaining the selected sample at the third temperature during a second predetermined duration; and
 c) starting heating from the third temperature by raising the temperature of the sample according to a third temperature gradient between 1° C./min and 50° C./min, up to a fourth temperature between 630° C. and 670° C.

8. The method according to claim 2, comprising determining the parameter representative of the quantity of hydrocarbon-containing compounds present in the first sample in both a free and a retained form by solving a formula:

$$HC_{Total,rock} = \frac{SurfQ_{rock}}{m_{rock} * TOC_{rock}}$$

wherein SurfQ$_{rock}$ corresponds to at least a part of an area under the measurement curve of the quantity of hydrocarbon-containing compounds released by the first sample, m$_{rock}$ which is an initial mass of the first sample, and TOC$_{rock}$ is the level of total organic carbon determined in the first sample.

9. The method according to claim 8, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein SurfQ$_{TOM}$ corresponds to at least a part of an area under the measurement curve of the quantity of hydrocarbon-containing compounds released by the second sample, m$_{TOM}$ which is an initial mass of the second sample, and TOC$_{TOM}$ is a level of total organic carbon determined for the second sample.

10. The method according to claim 8, comprising performing step A by heating a selected sample from the first sample and the second sample under an inert atmosphere comprising:
 a) starting heating from a first temperature between 50° C. and 120° C., raising the temperature of the selected sample according to a first temperature gradient between 1° C./min and 50° C./min, up to a second temperature between 180° C. and 220° C., and maintaining the selected sample at the second temperature for a first predetermined duration;
 b) starting heating from the second temperature, raising the temperature of the selected sample according to a second temperature gradient between 1° C./min and 50° C./min, up to a third temperature between 330° C. and 370° C., and maintaining the selected sample at the third temperature during a second predetermined duration; and
 c) starting heating from the third temperature by raising the temperature of the sample according to a third temperature gradient between 1° C./min and 50° C./min, up to a fourth temperature between 630° C. and 670° C.

11. The method according to claim 8, beginning at step a), maintaining the selected sample at the first temperature T1 for a duration between 2 and 6 minutes.

12. The method according to claim 2, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein SurfQ$_{TOM}$ corresponds to at least a part of an area under the measurement curve of the quantity of hydrocarbon-containing compounds released by the second sample, m$_{TOM}$ which is an initial mass of the second sample, and TOC$_{TOM}$ is a level of total organic carbon determined for the second sample.

13. The method according to claim 12, comprising performing step A by heating a selected sample from the first sample and the second sample under an inert atmosphere comprising:
 a) starting heating from a first temperature between 50° C. and 120° C., raising the temperature of the selected sample according to a first temperature gradient between 1° C./min and 50° C./min, up to a second temperature between 180° C. and 220° C., and maintaining the selected sample at the second temperature for a first predetermined duration;
 b) starting heating from the second temperature, raising the temperature of the selected sample according to a second temperature gradient between 1° C./min and 50° C./min, up to a third temperature between 330° C.

and 370° C., and maintaining the selected sample at the third temperature during a second predetermined duration; and c) starting heating from the third temperature by raising the temperature of the sample according to a third temperature gradient between 1° C./min and 50° C./min, up to a fourth temperature between 630° C. and 670° C.

14. The method according to claim 12, beginning at step a), maintaining the selected sample at the first temperature T1 for a duration between 2 and 6 minutes.

15. The method according to claim 2, comprising performing step A by heating a selected sample from the first sample and the second sample under an inert atmosphere comprising:

a) starting heating from a first temperature between 50° C. and 120° C., raising the temperature of the selected sample according to a first temperature gradient between 1° C./min and 50° C./min, up to a second temperature between 180° C. and 220° C., and maintaining the selected sample at the second temperature for a first predetermined duration;

b) starting heating from the second temperature, raising the temperature of the selected sample according to a second temperature gradient between 1° C./min and 50° C./min, up to a third temperature between 330° C. and 370° C., and maintaining the selected sample at the third temperature during a second predetermined duration; and c) starting heating from the third temperature by raising the temperature of the sample according to a third temperature gradient between 1° C./min and 50° C./min, up to a fourth temperature between 630° C. and 670° C.

16. The method according to claim 1, wherein the heating sequence in step B starts from a temperature between 200° C. and 400° C., and is raised according to a temperature gradient comprised between 20 and 40° C./minute, up to a temperature between 750 and 950° C.

17. The method according to claim 16, comprising determining the parameter representative of the quantity of hydrocarbon-containing compounds present in the first sample in both a free and a retained form by solving a formula:

$$HC_{Total,rock} = \frac{SurfQ_{rock}}{m_{rock} * TOC_{rock}}$$

wherein $SurfQ_{rock}$ corresponds to at least a part of an area under the measurement curve of the quantity of hydrocarbon-containing compounds released by the first sample, $m_{rock}$ which is an initial mass of the first sample, and $TOC_{rock}$ is the level of total organic carbon determined in the first sample.

18. The method according to claim 17, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein $Surf\,Q_{TOM}$ corresponds to at least a part of an area under the measurement curve of the quantity of hydrocarbon-containing compounds released by the second sample, $m_{TOM}$ which is an initial mass of the second sample, and $TOC_{TOM}$ is a level of total organic carbon determined for the second sample.

19. The method according to claim 16, comprising determining a parameter representative of the quantity of hydrocarbon-containing compounds present in the second sample in retained form by solving a formula:

$$HC_{Sorbed,TOM} = \frac{SurfQ_{TOM}}{m_{TOM} * TOC_{TOM}}$$

wherein $SurfQ_{TOM}$ corresponds to at least a part of an area under the measurement curve of the quantity of hydrocarbon-containing compounds released by the second sample, $m_{TOM}$ which is an initial mass of the second sample, and $TOC_{TOM}$ is a level of total organic carbon determined for the second sample.

20. The method according to claim 16, beginning at step a), maintaining the selected sample at the first temperature T1 for a duration between 2 and 6 minutes.

21. The method according to claim 1, comprising performing step A by heating a selected sample from the first sample and the second sample under an inert atmosphere comprising:

a) starting heating from a first temperature between 50° C. and 120° C., raising the temperature of the selected sample according to a first temperature gradient between 1° C./min and 50° C./min, up to a second temperature between 180° C. and 220° C., and maintaining the selected sample at the second temperature for a first predetermined duration;

b) starting heating from the second temperature, raising the temperature of the selected sample according to a second temperature gradient between 1° C./min and 50° C./min, up to a third temperature between 330° C. and 370° C., and maintaining the selected sample at the third temperature during a second predetermined duration; and c) starting heating from the third temperature by raising the temperature of the sample according to a third temperature gradient between 1° C./min and 50° C./min, up to a fourth temperature between 630° C. and 670° C.

22. The method according to claim 21, comprising, beginning at step a), maintaining the selected sample at the first temperature T1 for a duration between 2 and 6 minutes.

23. The method according to claim 22, beginning at step a), maintaining the selected sample at the first temperature T1 for a duration between 2 and 4 minutes.

24. The method according to claim 22, wherein the parameter representative of the quantity of hydrocarbon-containing compounds present in a free form in the first sample is determined by:

by solving a formula $$HC_{Total,rock}^{Shx} = \frac{SurfShx_{rock}}{m_{rock} * TOC_{rock}},$$

with Shx being selected from {Sh0, Sh1, Sh0+Sh1}, wherein $SurfSh0_{rock}$, $SurfSh1_{rock}$ and $SurfSh0+Sh1_{rock}$ correspond respectively to an area under a measurement curve of the quantity of hydrocarbon-containing compounds released by the first sample between the first and second temperatures, the second and third temperatures, and the first and third temperatures.

25. The method according to claim 24, wherein the parameter representative of the quantity of hydrocarbon-containing compounds present in free form in the sedimentary rock is determined by solving a formula wherein:

$$HC_{Free}^{Shx} = HC_{Total,rock}^{Shx} - HC_{Sorbed,TOM}^{Shx}, \text{with Shx selected from } \{Sh0, Sh1, Sh0+Sh1\}.$$

26. The method according to claim 25, wherein a parameter representative of a proportion of a quantity of hydrocarbon-containing compounds present in a free form is also determined with respect to a quantity of hydrocarbon-containing compounds present in retained form in the sedimentary rock by solving a formula:

$$\% HC_{Free}^{Shx} = HC_{Free}^{Shx} / HC_{Total,rock}^{Shx} * 100, \text{with Shx selected from } \{Sh0, Sh1, Sh0+Sh1\}.$$

27. The method according to claim 21, beginning at step a), maintaining the selected sample at the first temperature T1 for a duration between 2 and 4 minutes.

28. The method according to claim 27, wherein the parameter representative of the quantity of hydrocarbon-containing compounds present in a free form in the first sample is determined by:
by solving a formula $$HC_{Total,rock}^{Shx} = \frac{SurfShx_{rock}}{m_{rock} * TOC_{rock}},$$

with Shx being selected from $\{Sh0, Sh1, Sh0+Sh1\}$, wherein $SurfSh0_{rock}$, $SurfSh1_{rock}$ and $SurfSh0+Sh1_{rock}$ correspond respectively to an area under a measurement curve of the quantity of hydrocarbon-containing compounds released by the first sample between the first and second temperatures, the second and third temperatures, and the first and third temperatures.

29. The method according to claim 28, wherein the parameter representative of the quantity of hydrocarbon-containing compounds present in free form in the sedimentary rock is determined by solving a formula:

$$HC_{Free}^{Shx} = HC_{Total,rock}^{Shx} - HC_{Sorbed,TOM}^{Shx}, \text{with Shx selected from } \{Sh0, Sh1, Sh0+Sh1\}.$$

30. The method according to claim 29, wherein a parameter representative of a proportion of a quantity of hydrocarbon-containing compounds present in free form is also determined with respect to a quantity of hydrocarbon-containing compounds present in retained form in the sedimentary rock by solving a formula:

$$\% HC_{Free}^{Shx} = HC_{Free}^{Shx} / HC_{Total,rock}^{Shx} * 100, \text{with Shx selected from } \{Sh0, Sh1, Sh0+Sh1\}.$$

31. The method according to claim 21, wherein the parameter representative of the quantity of hydrocarbon-containing compounds present in a free form in the first sample is determined by:
by solving a formula $$HC_{Total,rock}^{Shx} = \frac{SurfShx_{rock}}{m_{rock} * TOC_{rock}},$$

with Shx being selected from $\{Sh0, Sh1, Sh0+Sh1\}$, wherein $SurfSh0_{rock}$, $SurfSh1_{rock}$ and $SurfSh0+Sh1_{rock}$ correspond respectively to an area under a measurement curve of the quantity of hydrocarbon-containing compounds released by the first sample between the first and second temperatures, the second and third temperatures, and the first and third temperatures.

32. The method according to claim 31, wherein the parameter representative of the quantity of hydrocarbon-containing compounds present in free form in the sedimentary rock is determined by solving a formula wherein:

$$HC_{Free}^{Shx} = HC_{Total,rock}^{Shx} - HC_{Sorbed,TOM}^{Shx}, \text{with Shx selected from } \{Sh0, Sh1, Sh0+Sh1\}.$$

33. The method according to claim 32, wherein a parameter representative of a proportion of the quantity of hydrocarbon-containing compounds present in a free form with respect to the quantity of hydrocarbon-containing compounds present in retained form in the sedimentary rock is determined by solving a formula:

$$\% HC_{Free}^{Shx} = HC_{Free}^{Shx} / HC_{Total,rock}^{Shx} * 100, \text{with Shx selected from } \{Sh0, Sh1, Sh0+Sh1\}.$$

* * * * *